US012805962B1

(12) United States Patent
Rackers et al.

(10) Patent No.: US 12,805,962 B1
(45) Date of Patent: Nov. 24, 2026

(54) STERILE SURGICAL DRAPE WITH INTEGRATED ATTACHMENT SYSTEM FOR UNATTENDED SLUSH PRODUCTION

(71) Applicant: WEG Surgical Solutions, LLC, Greensboro, NC (US)

(72) Inventors: Kevin J. Rackers, Summerfield, NC (US); Patrick S. Lee, Greensboro, NC (US); Benjamin A. Perrot, Greensboro, NC (US); Thomas J. Wanbaugh, Apex, NC (US); Paul Grozier, Libertyville, IL (US)

(73) Assignee: WEG Surgical Solutions, LLC, Greensboro, NC (US)

( * ) Notice: Subject to any disclaimer, the term of this patent is extended or adjusted under 35 U.S.C. 154(b) by 0 days.

(21) Appl. No.: 19/642,576

(22) Filed: Apr. 8, 2026

(51) Int. Cl.
*A61B 46/10* (2016.01)

(52) U.S. Cl.
CPC .................................... *A61B 46/10* (2016.02)

(58) Field of Classification Search
CPC .................................. A61B 46/10; F25C 1/00
See application file for complete search history.

(56) References Cited

U.S. PATENT DOCUMENTS 2,051,407 A 8/1936 Jones
4,011,635 A 3/1977 Meyer
4,409,706 A 10/1983 Clendinen
4,646,399 A 3/1987 Clendinen
4,934,152 A 6/1990 Templeton
5,331,820 A 7/1994 Faries, Jr. et al.
5,400,516 A 3/1995 Kellenberger
5,457,962 A 10/1995 Faries, Jr. et al.
5,502,980 A 4/1996 Faries, Jr. et al.
6,003,328 A 12/1999 Faries, Jr. et al.
6,035,855 A 3/2000 Faries, Jr. et al.
6,091,058 A * 7/2000 Faries, Jr. .............. A61B 46/10 604/114
7,350,373 B1 4/2008 Faries, Jr. et al.
7,874,167 B2 1/2011 Kammer et al.
9,549,843 B2 1/2017 Kammer et al.
9,561,895 B1 2/2017 Kammer et al.
9,693,892 B1 7/2017 Kammer et al.
10,231,866 B1 3/2019 Kammer et al.
(Continued)

*Primary Examiner* — Camtu T Nguyen
(74) *Attorney, Agent, or Firm* — ePatentManager.com; Guerry L. Grune

(57) ABSTRACT

A sterile drape assembly for use with a surgical slush production machine enables unattended slush production while maintaining sterile technique protocols. The drape assembly has a flexible sterile drape sized to conform to a refrigerated basin, a rigid disk attached to the drape center for coupling with a lifting mechanism, and one or more clip attachments secured to the underside of the drape. The clips releasably engage with studs mounted on the machine's top surface. The studs include a base, post, and head, with clips having flexible tabs which engage around the post or an aperture configured to engage rotationally with the studs resisting lateral movement of drapes during cyclic lifting operations, preventing the drape from bunching up under the disk with proper heat transfer throughout the slush production cycle. The clips are engaged by touching only on the drape's top surface while also complying with AORN sterile technique guidelines.

12 Claims, 11 Drawing Sheets

(56) References Cited

U.S. PATENT DOCUMENTS

| | | | |
|---|---|---|---|
| 10,575,984 | B2 | 3/2020 | Kammer et al. |
| 10,973,601 | B2 | 4/2021 | Rackers et al. |
| 12,290,332 | B2 | 5/2025 | Rackers et al. |
| 2011/0123294 | A1 | 5/2011 | Kempf et al. |
| 2017/0086934 | A1 | 3/2017 | Devengenzo et al. |
| 2019/0264725 | A1 | 8/2019 | Forti |
| 2024/0268913 | A1 | 8/2024 | White et al. |

* cited by examiner

STERILE SURGICAL DRAPE WITH INTEGRATED ATTACHMENT SYSTEM FOR UNATTENDED SLUSH PRODUCTION

FIELD

The present disclosure relates generally to sterile surgical drapes, and more particularly to a sterile drape assembly with an integrated attachment system for use in surgical slush production machines that enables unattended slush production while maintaining sterile technique protocols.

BACKGROUND

Sterile saline slush is used in a variety of surgical procedures to slow organ and tissue metabolic rates. A common machine for producing slush includes a refrigeration system that cools the surface of a metal basin. The machine and metal basin are non-sterile. A sterile drape is placed so it covers the machine and lines the surface of the metal basin. Sterile liquid saline is poured into the drape-lined basin. When the machine cools the basin walls, heat is drawn out of the saline while the drape provides a sterile barrier.

The Templeton patent (U.S. Pat. No. 4,934,152) discloses a surgical slush producing system having a lower cabinet containing a refrigeration system that cools a basin at the top of the cabinet to a temperature below the freezing point of a sterile liquid that is to be turned into a slush consistency. A sterilized drape is placed over the device and is sufficiently flexible to allow it to conform to the interior shape of the basin. The sterile fluid is poured into the drape-lined basin. A refrigeration system cools the basin and heat is removed from the sterile fluid through the flexible drape. As this heat transfer process continues, the sterile fluid eventually reaches its freezing point and begins to freeze to the drape that is in contact with the cooled basin. The user must manually dislodge the frozen solution from the drape so that it does not form hard clumps and so that liquid that is not yet frozen can contact the cooled drape. By repeatedly manually dislodging the frozen solution from the wall, slush can be formed that is smooth and without large, hard clumps.

The Faries, Jr. et al. patent (U.S. Pat. No. 5,331,820) discloses several methods for automatically manipulating the drape relative to the basin wall to cause the collected congealed solution to be dislodged from the walls. One method described in this patent has become common in slush machines over the last couple decades. This method involves cyclically lifting and lowering a disk that is attached to the sterile drape while heat is removed from the sterile liquid through the basin wall. When the mechanism is in the lowered position, the fluid-filled drape is contacting the chilled basin walls and through this contact the solution freezes. The mechanism then lifts the disk and drape which causes the drape to flex and deform. This action causes small clumps of the frozen solution to be dislodged from the drape and then to float away from the drape and into the bulk liquid or slush solution.

U.S. Pat. No. 5,457,962 (Faries, Jr. et al., 1995) is a continuation that bonds a disk or plate directly to the underside of the drape via adhesive or welding, so the drape-disk is a self-contained sterile assembly. The disk snaps onto the machine's drive plate below the basin.

However, this engagement is at the basin floor level (a non-sterile zone), not on the top surface of the machine. This patent does not constrain lateral drape movement at the machine rim.

U.S. Pat. No. 5,502,980 (Faries, Jr. et al., 1996) is a continuation-in-part of U.S. Pat. No. 5,457,962, further optimizing the bonded-disk drape with fittings to engage the cyclically movable machine shaft. This patent considers rotational, wobble, and vertical reciprocating motion but does not address drape migration at the perimeter. All securement occurs at the basin center (drive shaft), not at the machine top surface perimeter.

U.S. Pat. No. 7,350,373 (Faries, Jr. et al., 2008) discloses a surgical disk drape with a two-part disk (base and cover) bonded to opposing surfaces of the drape. The disk includes an engagement member for attaching to the machine dislodgment mechanism, which may be a snap-fit or friction fit. While this patent explicitly mentions snap-fit engagement between the drape disk and the machine shaft component, this engagement is only at the basin center for the drive mechanism—not at the top surface for perimeter drape constraint. The problem of drape migration during cyclic operation is not addressed.

Competitor patents from C Change Surgical (U.S. Pat. Nos. 7,874,167; 9,549,843; 9,561,895; 9,693,892; 10,231,866; and 10,575,984) address methods for producing well-mixed slush, use of sterile sleeves, oscillation techniques, and complex rotational motion. These patents focus on motion mechanics and slush quality but do not address lateral drape constraint via a top-surface fastener system. None of these patents discloses a stud and clip engagement on the machine top surface to anchor the drape perimeter.

While snap fastener technology is well-known in the art (e.g., U.S. Pat. Nos. 4,409,706 and 4,646,399), and surgical drapes with integrated fasteners exist for robotic cart applications (U.S. Patent Application Publication No. 2017/0086934), no known art combines these concepts for a slush basin drape with perimeter lateral restraint on the machine top surface. All known art drape securements for the slush machine field addresses only center-of-drape engagement with the drive shaft inside the basin-none provides mechanical restraint at the machine top surface perimeter while adhering to sterile draping practices so as to prevent the drape from being pulled into the basin during cyclic operation.

Previous attempts to address the drape migration problem have included the use of adhesive tape to secure the drape to the machine surface. However, tape-based attachment systems have significant drawbacks. Adhesive tape does not provide a reliable, repeatable attachment and can lose adhesion when exposed to moisture from condensation. Proper positioning of a drape with adhesive tape would be extremely difficult if not impossible because the tape backing would need to be removed from all strips of adhesive before placing the drape. Properly placing one of the multiple strips is likely to cause other exposed adhesive strips to adhere to the base of slush producing machine in an incorrect location or to improperly adhere to the drape itself. Furthermore, adhesive residue left on the machine surface after tape removal is difficult to clean and can harbor contaminants, complicating infection control protocols.

Other prior attempts have employed fixed pegs or posts positioned around the basin perimeter, with corresponding holes or grommets in the drape that are placed over the pegs. However, a peg-based system has a critical deficiency. Having an opening or hole in a portion of the drape that covers a non-sterile surface would compromise the sterility of the draped surface. Placing a cap over each stud to hold the drape in place would cover the non-sterile peg, but drape sterility will have already been compromised during drape placement.

Neither tape nor peg-based systems provide the combination of positive mechanical retention, sterility-compliant installation from the top surface only, and reliable performance throughout the slush production cycle that is required for truly unattended slush production.

However, if the drape is placed in an improper position in the machine or if it moves out of a proper position due to the up/down cycling of the drape, the slush produced can have hard clumps or sharp edges that make it unusable for its intended purpose. A machine that is left unattended during slush production will eventually get to a condition where the drape bunches up under the rigid disk. This occurs because the up and down movement of the rigid disk along with the fluid/slush weight tends to cause a force along the drape that drags it into the basin. When this occurs, ice formed at the wall does not break free from the drape/wall interface and it continues to build up until there are hard frozen chunks of saline at the walls.

To overcome this shortcoming with current systems, a nurse must attend the machine every few minutes to manipulate the drape and put it back into a proper location. This is not too difficult to do in the early stage of slush production when there is only liquid in the basin because the clear liquid makes it easy to see when the drape is in the proper condition. However, when there is some slush in the basin, the bottom of the drape cannot be seen, and it is extremely difficult to ensure the drape is not left in an improper position.

Attempts to solve this problem have been introduced over the years. However, previous attempts have several drawbacks in that they either did not fully constrain the drape in a proper position or required the drape to be secured along the side of the machine. The issue with constraining the drape to the side of the machine is that it can violate sterility protocols in many hospitals. The typical protocols prohibit a nurse in the sterile field from touching the portion of a drape that extends below the top of a draped surface.

Additionally, the Association of periOperative Registered Nurses (AORN) Guidelines for Perioperative Practice, Guideline for Sterile Technique, Section 4.2.5 recommends: “Do not move the portion of the sterile surgical drape that establishes the sterile field after initial placement.” Furthermore, Section 4.3 states that areas below the level of the instrument tabletop and the OR bed should be considered contaminated, and items that move to a position below the level of the sterile field should be considered contaminated.

Furthermore, established principles of sterile technique provide that: (1) a sterile field is established for each surgical procedure; (2) once sterile drapes have been placed, they should not be repositioned; (3) any item extending or falling below the table edge is considered non-sterile; and (4) the top of a sterile, draped table is the only portion that is considered sterile. When applying these principles, the part of a sterile cover or drape extending below the edge of the sterile table is non-sterile because only the top of the draped table is considered sterile. These principles create significant constraints on how a drape securement system can be designed and installed while maintaining sterility.

There is therefore a need for a sterile drape assembly that can be secured to a slush machine in a manner that maintains proper drape positioning throughout the slush production cycle, enables unattended slush production, and complies with sterile technique protocols by allowing attachment without requiring contact with portions of the drape below the top surface of the machine.

SUMMARY

The present disclosure overcomes the drape placement shortcoming with current systems and allows for the unattended production of surgical slush while maintaining proper sterility techniques. Unlike prior art systems that provide drape securement only at the basin center (drive shaft engagement), the present disclosure is the first to provide a mechanical restraint system that can be engaged with a sterile draping method at the top surface perimeter of the machine specifically to prevent the drape from being pulled into the basin during cyclic operation. This is accomplished by integrating attachment elements to the underside of the drape which interface with corresponding attachment points on the slush machine top surface. The attachments can be made after the drape is placed on the machine with a sterile placement technique. Critically, the attachments can be made by only touching the top surface of the machine with no need to touch the drape below the top surface, thereby complying with AORN Guidelines Section 4.2.5 which recommends not moving the portion of the sterile surgical drape that establishes the sterile field after initial placement, and Section 4.3 which considers areas below the level of the instrument tabletop to be contaminated. This sterility-protocol constraint driving the top-surface-only fastener placement is a clinically motivated design choice not found in any prior art. The present disclosure recognizes that the top of a sterile, draped table is the only portion considered sterile, and that any portion of the drape extending below the table edge is non-sterile. By placing the engagement system on the machine top surface and designing clips to be engaged downward from above, the disclosure ensures that the sterile field is never compromised during installation. Unlike prior art tape-based systems that can fail due to moisture exposure, and unlike peg-based systems that require sterility-compromising installation procedures, the clip and stud system of the present disclosure provides reliable mechanical engagement that maintains drape position throughout the entire slush production cycle while enabling installation entirely from the sterile top surface of the machine.

In one aspect, the present disclosure provides a sterile drape assembly for use with a surgical slush production machine having a basin and a lifting mechanism. The drape assembly comprises a flexible sterile drape sized to conform to an interior surface of the basin, a rigid disk attached to a central portion of the flexible sterile drape and configured to couple with the lifting mechanism, and one or more one or more clip attachments secured to an underside of the flexible sterile drape at positions radially outward from the rigid disk. Each clip attachment is configured to releasably engage with a corresponding stud mounted on a top surface of the slush production machine to resist lateral movement of the drape during operation of the lifting mechanism.

In another aspect, the present disclosure provides a surgical slush production system comprising a machine cabinet having a refrigeration system, a basin mounted at a top portion of the machine cabinet and configured to be cooled by the refrigeration system, a lifting mechanism having a lifting rod extending into the basin, one or more studs mounted on a top surface of the machine cabinet surrounding the basin, and a sterile drape assembly. The sterile drape assembly includes a flexible sterile drape, a rigid disk attached to the drape and coupled to the lifting rod, and one or more clips attached to the underside of the drape and engaged with the studs to maintain the drape in a proper position during cyclic operation of the lifting mechanism.

In yet another aspect, the present disclosure provides a method of producing sterile surgical slush without operator intervention comprising the steps of placing a sterile drape assembly over a slush production machine, engaging clip attachments on the drape with studs on the machine top surface, pouring sterile saline into the drape-lined basin, and operating the machine to produce slush while the clips maintain the drape in proper position.

In still another aspect, the present disclosure provides a method of installing a sterile drape on a surgical slush machine while maintaining sterile technique comprising positioning the drape over the machine, coupling the rigid disk to the lifting rod, and engaging the clips with the studs without touching any portion of the drape below the top surface of the machine.

More specifically the present disclosure provides a sterile drape assembly for use with a surgical slush production machine having a basin configured to hold a sterile liquid and a lifting mechanism, the drape assembly comprising:

a flexible sterile drape sized and configured to conform to an interior surface of the basin;

a rigid disk attached to a central portion of the flexible sterile drape, the rigid disk configured to releasably couple with the lifting mechanism; and one or more clip attachments secured to an underside of the flexible sterile drape at positions radially outward from the rigid disk, each of the clip attachments configured to releasably engage with a corresponding attachment point on a top surface of the slush production machine to resist lateral movement of the drape during cyclic operation of the lifting mechanism.

Here, each of the clip attachments comprises a body having a central aperture and one or more of flexible tabs extending from the central aperture, the tabs configured to flex outwardly when pressed over an attachment point and return to an original position to engage the attachment point.

In at least one embodiment, the flexible tabs have curved edges that form segments of a circle having a diameter smaller than a head diameter of the attachment point and approximately equal to a post diameter of the attachment point.

In yet another embodiment, the one or more clip attachments comprises four clip attachments arranged symmetrically about the rigid disk.

Here, the clip attachments are heat sealed, glued, or attached with adhesive tape to the underside of the flexible sterile drape.

In many embodiments the rigid disk has a circular shape and includes a central coupling mechanism configured to snap onto a lifting rod of the lifting mechanism.

It is also possible that the flexible sterile drape is transparent.

In many arrangements, the clip attachments are positioned on the drape such that when the drape is placed over the slush production machine, each of the clip attachments aligns with a corresponding stud mounted on the top surface of the machine surrounding the basin.

The clip attachments are configured to be engaged with the attachment points by pressing downward on a top surface of the drape without requiring contact with any portion of the drape below the top surface of the machine.

Here and in other embodiments, the clip attachments and the rigid disk are integrally formed as a unitary component that is attached to the flexible sterile drape.

In a further embodiment a surgical slush production system comprises;

a machine cabinet having a refrigeration system;

a basin mounted at a top portion of the machine cabinet and configured to be cooled by the refrigeration system to a temperature below a freezing point of a sterile liquid;

a lifting mechanism having a lifting rod extending into the basin, the lifting mechanism configured to cyclically raise and lower the lifting rod;

one or more studs mounted on a top surface of the machine cabinet at positions surrounding the basin, each of the studs having a base, a post extending from the base, and a head having a geometry larger than the post; and a sterile drape assembly comprising:

a flexible sterile drape sized to conform to an interior surface of the basin, a rigid disk attached to the flexible sterile drape and coupled to the lifting rod, and one or more clip attachments secured to an underside of the flexible sterile drape and engaged with the studs to maintain the drape in a proper position during cyclic operation of the lifting mechanism.

In this embodiment and others the head of each of the studs is spherical.

It is also that the head of each of the button studs has a polygon or pyramid shape.

The surgical slush production system can also include the fact that each of the clip attachments comprises flexible tabs configured to flex over the head of the stud and engage around the post.

In this and other embodiments, the one or more studs comprises four studs arranged symmetrically around the basin.

For this and additional embodiments, the machine cabinet includes casters for mobility and ventilation openings for the refrigeration system.

In many cases, the basin has angled walls tapering downward toward a center.

In this and other embodiments can include a refrigerant tubing wrapped around an underside of the basin to form evaporator tubing for cooling the basin.

Here, the clip attachments resist lateral movement of the drape caused by cyclic operation of the lifting mechanism while permitting vertical movement for engagement and disengagement of the clip attachments with the studs.

For the surgical slush production of the present system, the clip attachments are positioned such that engagement with the studs can be accomplished by pressing downward on a top surface of the drape without touching any portion of the drape below the top surface of the machine cabinet.

The proper position maintained by the clip attachments engaged with the studs causes the flexible sterile drape to contact the basin walls when the lifting rod is in a lowered position and to flex away from the basin walls when the lifting rod is in a raised position.

In yet another embodiment, a method of producing sterile surgical slush without operator intervention is included, the method comprising:

providing a slush production machine having a refrigerated basin, a lifting mechanism with a lifting rod, and one or more studs mounted on a top surface of the machine surrounding the basin;

placing a sterile drape assembly over the machine, the drape assembly having a flexible sterile drape, a rigid disk attached to the drape, and one or more clip attachments secured to an underside of the drape;

coupling the rigid disk to the lifting rod;

engaging the clip attachments with the studs to secure the drape in a proper position;

pouring sterile liquid into the drape-lined basin; and operating the lifting mechanism to cyclically raise and lower the rigid disk and the drape while the refrigerated basin cools the sterile liquid to produce slush, wherein the clip attachments engaged with the studs maintain the drape in the proper position throughout a slush production cycle without requiring operator intervention to reposition the drape.

Here, the engaging step comprises pressing downward on a top surface of the drape at locations above the clip attachments to cause the clip attachments to snap over the studs.

Once in the proper position causes the flexible sterile drape to contact walls of the basin when the lifting rod is in a lowered position, enabling heat transfer from the sterile liquid through the drape to the refrigerated basin.

This proper position causes the flexible sterile drape to flex away from walls of the basin when the lifting rod is in a raised position, causing frozen crystals to be dislodged from the drape.

In this and other embodiments removing the drape assembly after slush production by pulling upward on the drape with sufficient force to disengage the clip attachments from the studs is desired.

In a further embodiment a method of installing a sterile drape on a surgical slush machine while maintaining sterile technique is included, the method comprising:

- providing a sterile drape assembly having a flexible sterile drape, a rigid disk attached to a central portion of the drape, and one or more clip attachments secured to an underside of the drape at positions radially outward from the rigid disk;
- positioning the sterile drape assembly over a slush machine having a basin, a lifting rod, and one or more studs on a top surface of the machine;
- coupling the rigid disk to the lifting rod; and
- engaging the clip attachments with the studs by touching a top surface of the drape without touching any portion of the drape below the top surface of the machine, thereby maintaining compliance with sterile technique protocols.

Here, the sterile technique protocols include a recommendation not to move a portion of a sterile surgical drape that establishes a sterile field after initial placement.

In this and other embodiments, the sterile technique protocols include considering areas below a level of an instrument tabletop to be contaminated.

Here, the engaging step is performed by a scrubbed team member without the scrubbed team member reaching over an unsterile area or contacting an unsterile surface.

In this and other embodiments, the clip attachments comprise flexible tabs that flex outwardly when pressed over heads of the studs and return to an original position to engage posts of the studs.

Here, the one or more clip attachments comprises one or more clip attachments, each clip attachment configured to engage a corresponding cross post on the top surface of the slush production machine by rotation.

In this and other embodiments, the cross post comprises a vertical post with a horizontal pin extending therefrom, and the clip attachment comprises a slot configured to receive the horizontal pin when the clip attachment is rotated into a locked position.

BRIEF DESCRIPTION

Figure 10A:
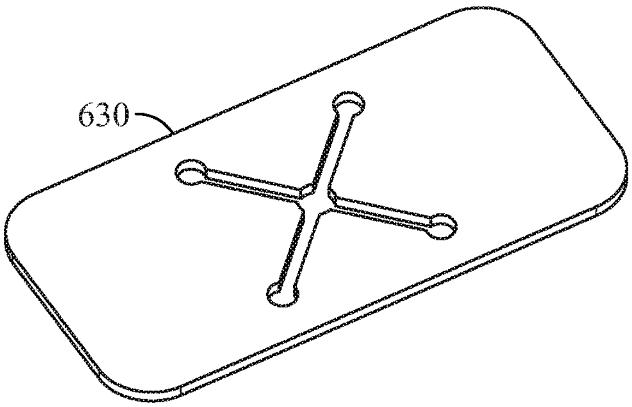
Figure 10B:
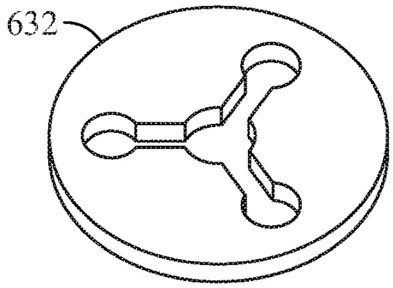
Figure 10C:
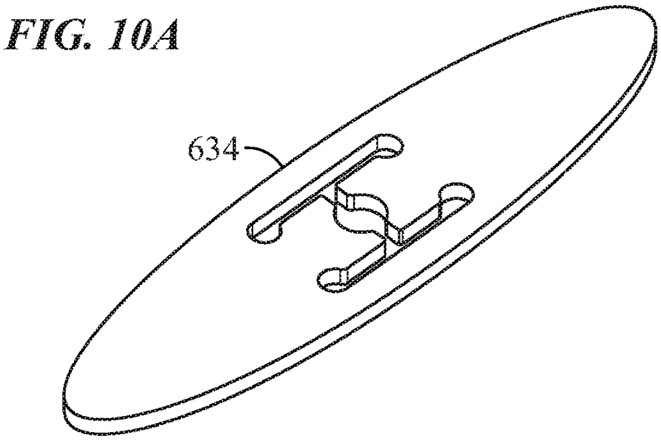

FIGS. 10A, 10B, and 10C show alternative snap-clip embodiments, illustrating various tab configurations that can engage with the button stud or the polygon stud.

Figure 11A:
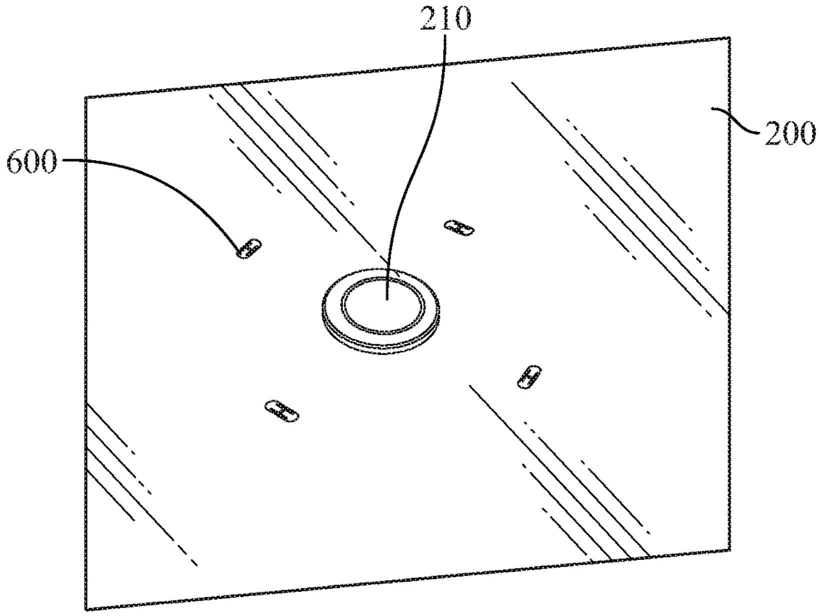

FIG. 11A is a top-down view of a transparent sterile drape laid flat showing the central rigid disk and snap-clip attachments secured to the underside of the drape.

Figure 11B:
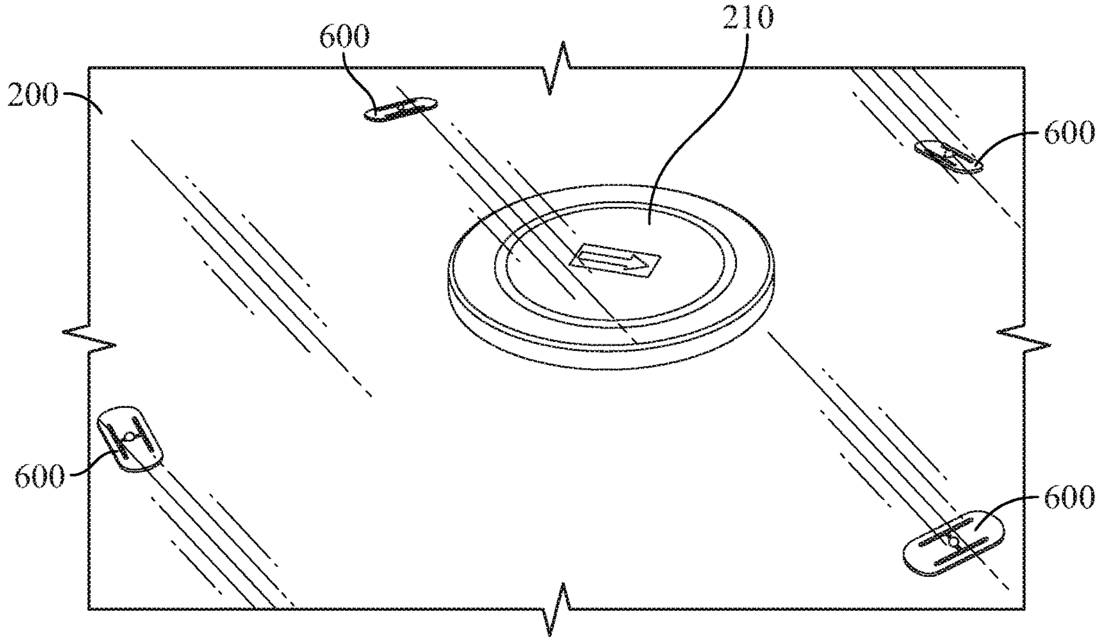

FIG. 11B provides a close-up view of the central rigid disk and snap-clip attachments secured to the underside of the drape.

Figure 12A:
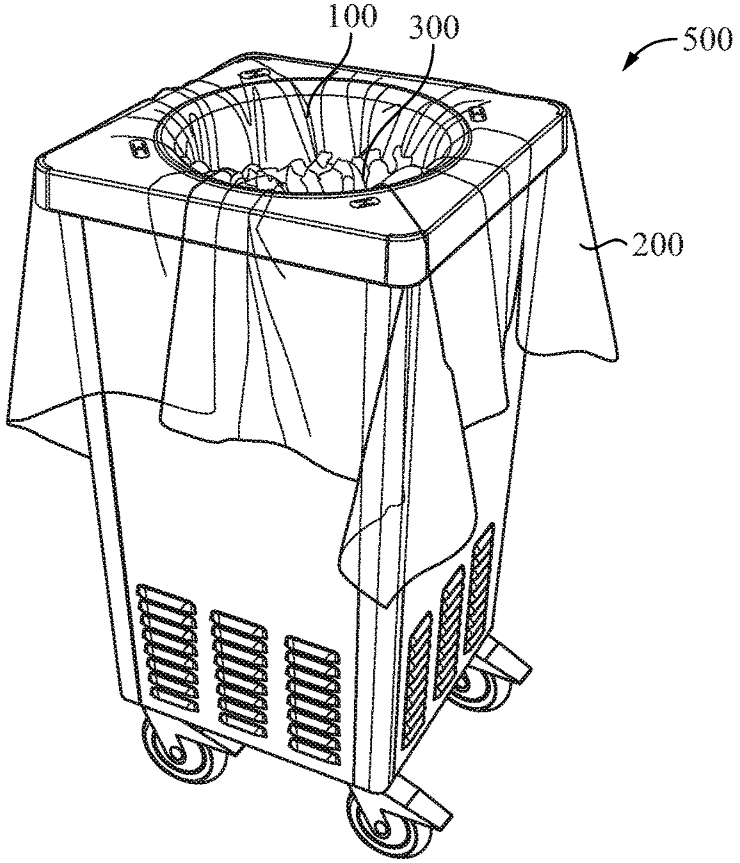
Figure 12B:
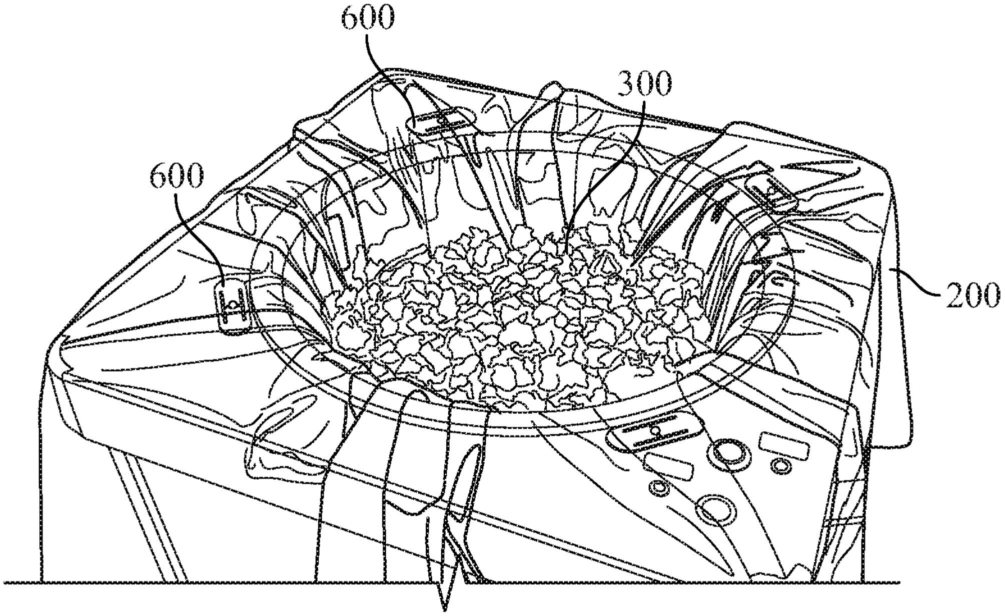
Figure 12C:
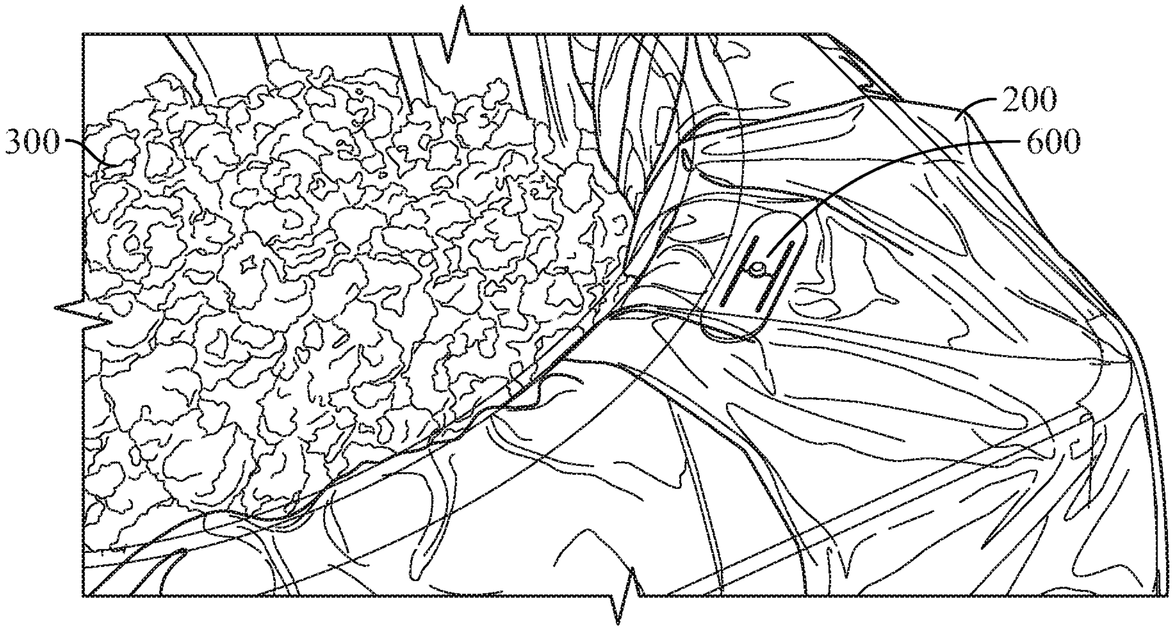

FIGS. 12A, 12B, and 12C are taken from photographs showing the slush machine in operation with the sterile drape properly installed and filled with saline slush.

DETAILED DESCRIPTION

Figure 1:
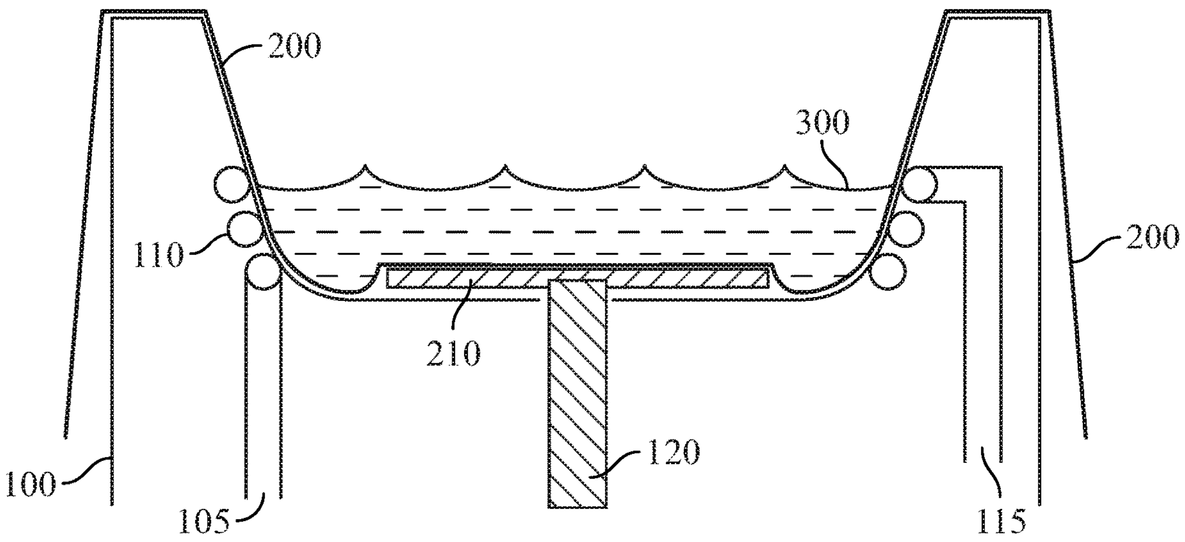
FIG. 1 is a cross-sectional view of a slush machine showing the machine frame with integral basin, refrigerant tubing, flexible drape, rigid disk, lifting rod, and saline fluid in a lowered position.
Figure 2:
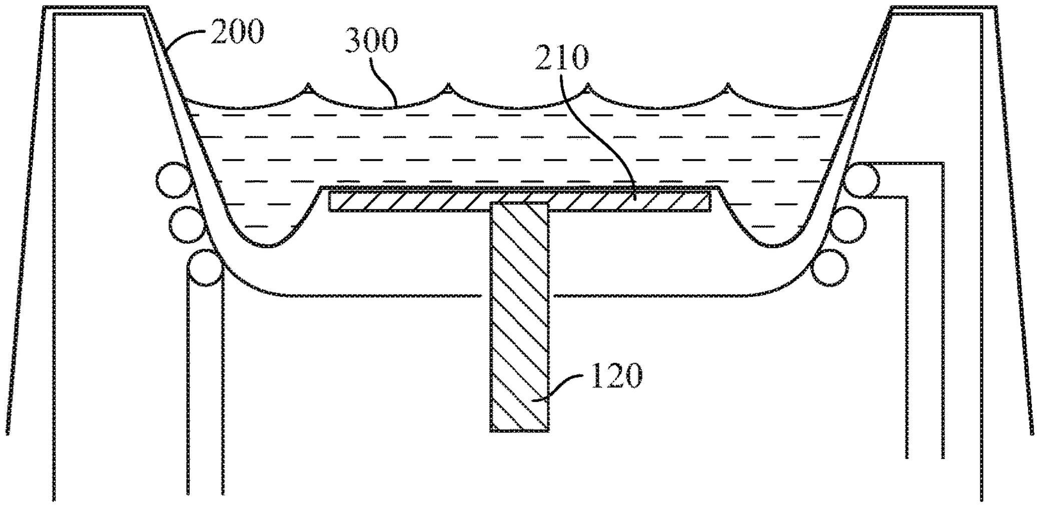
FIG. 2 is a cross-sectional view of the slush machine of FIG. 1 showing the lifting rod and disk in a raised position with the drape flexed away from the basin walls.

Referring now to the drawings, wherein reference numerals designate like or corresponding parts throughout the several views, FIGS. 1 and 2 illustrate the basic components and operation of a slush machine.

Referring to FIGS. 1 and 2, cross-sectional views of slush machines are shown illustrating the basic components and operation. A machine frame with integral basin 100 contains a recessed basin sized to hold a volume of saline solution. Refrigerant supply tubing 105 from a refrigeration system (not shown) is wrapped around the underside of the basin 100 to form evaporator tubing 110. A refrigerant is pumped through the supply tubing 105 by the refrigeration system and flows around the evaporator tubing 110 to cool the basin 100. After cooling the basin 100, the refrigerant exits the evaporator tubing 110 and flows back to the refrigeration system through return tubing 115. A flexible drape 200 is placed over the frame and the basin 100 and allowed to conform to the inner walls of the basin 100. The drape 200 contains a rigid disk 210 that is attached to the drape 200. The disk 210 is coupled to a lifting rod 120. Saline fluid 300 is poured in the basin 100 and is prevented from directly contacting the basin 100 by the sterile drape 200.

In FIG. 1, the lifting rod 120 is shown in the lowered position where the fluid-filled drape 200 contacts the chilled basin walls, enabling heat transfer from the saline through the drape 200 to the refrigerated basin surface. In FIG. 2, the lifting rod 120 is shown in the raised or upper position. The rod 120 is moved up and down by a lifting mechanism (not shown). While the lifting rod 120 is in the upper position, the disk 210 is lifted upward and the drape 200 flexes and moves away from the basin wall. The elevation of the fluid 300 is raised relative to the basin 100. The flexing of the drape 200 and the movement of the fluid 300 tends to make any solid ice crystals release from the drape 200.

During the slush formation process, the ice crystals are moved away from the heat transfer surface where cooling occurs. This prevents the crystals from forming large hard chunks and helps maintain a smooth textured slush. Early in the process, while most of the saline is in liquid form, the crystals that are released from the drape 200 will float into the liquid and melt as they transfer heat to cool the bulk fluid. When the bulk fluid finally reaches the freezing point, energy removed from the saline goes toward the phase change from liquid to solid. The motion of the lifting rod 120 tends to mix the slush and helps to circulate the liquid in the slush mixture so it can contact the walls and change phase.

Figure 3:
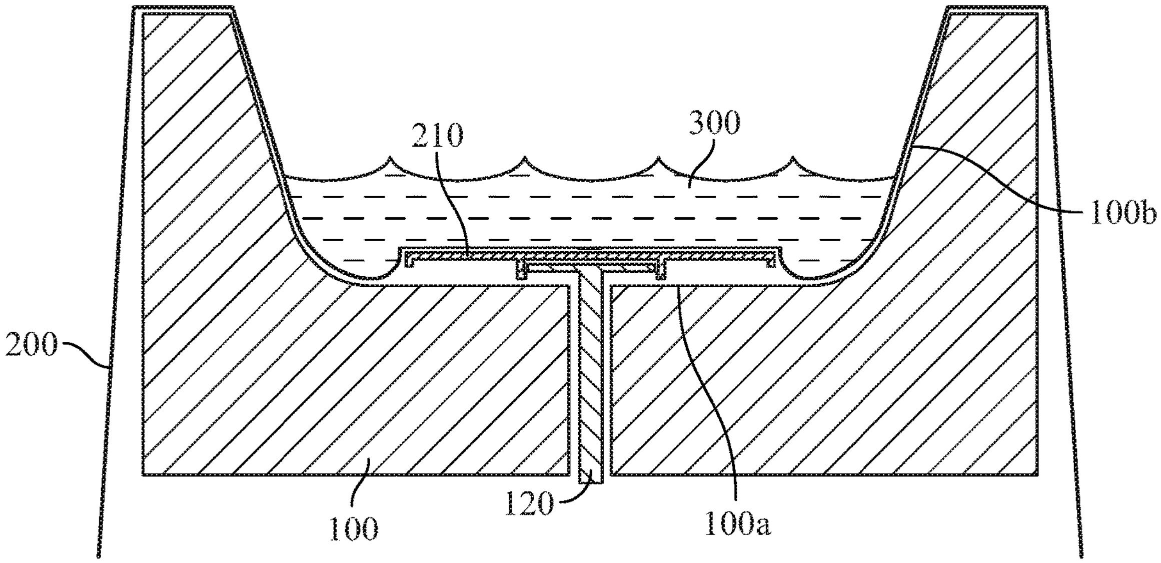
FIG. 3 is a cross-sectional view showing a properly positioned drape in a lowered position where the drape contacts the basin bottom and walls for effective heat transfer.

Referring to FIG. 3, a cross-sectional view showing a properly positioned drape is illustrated. When the drape 200 is properly placed, the flexible drape material hangs down at the perimeter of the rigid disk 210 so it contacts the basin bottom and walls. This proper positioning ensures effective heat transfer between the saline fluid and the refrigerated basin walls through the drape 200 material. The rigid disk 210 is heat sealed to the bottom of the drape 200 and is designed so it snaps onto the lifting rod 120 of the machine.

Figure 4:
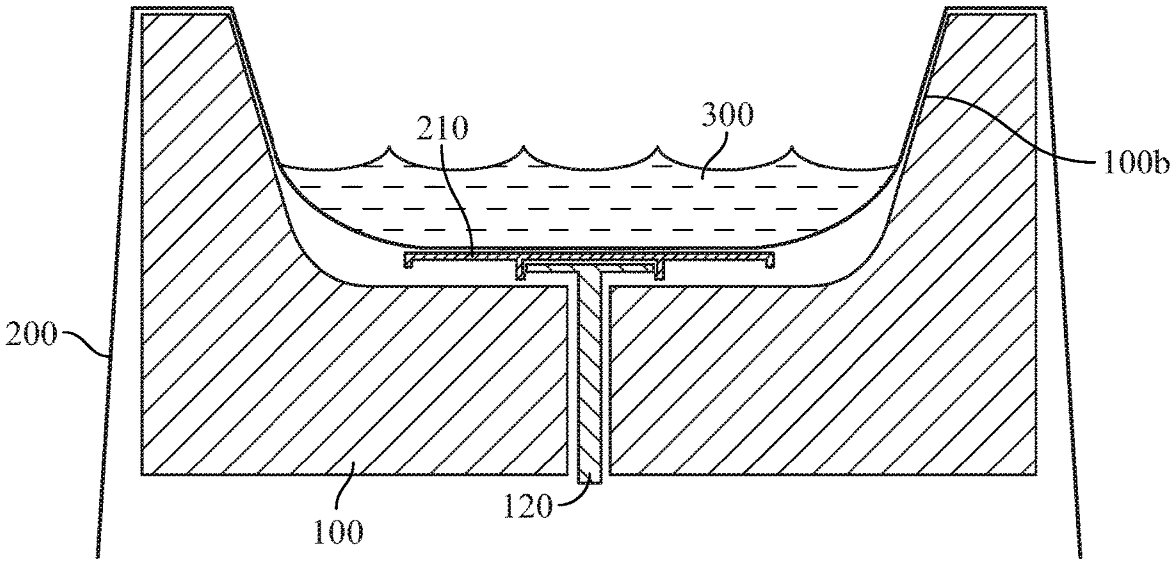
FIG. 4 is a cross-sectional view showing an improperly placed drape where the fluid is not contacting the walls of the basin while the disk is in the down position.

Referring to FIG. 4, an improperly placed drape condition is shown where the fluid is not contacting the walls of the basin while the disk is in the down position. If the drape 200 were placed as shown, the drape 200 would hold the saline fluid 300 away from the refrigerated basin wall 100*b* in both the up and down position of the lifting rod 120 and the corresponding rigid disk 210. There will be minimal heat transferred out of the fluid which would result in either an extremely long time to produce slush or no slush production at all if heat loss to ambient were greater than the convective heat removal through the liquid-drape-air-basin heat transfer path.

Figure 5A:
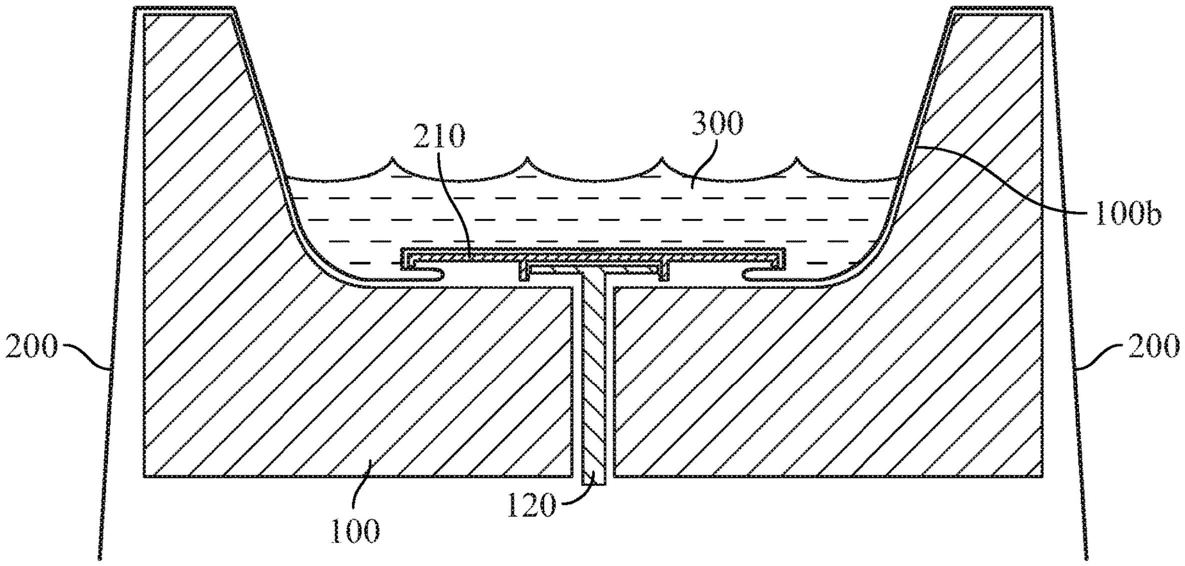
FIG. 5A is a cross-sectional view showing an improperly placed drape where the drape has bunched up beneath the rigid disk, with the lifting mechanism in the down position.
Figure 5B:
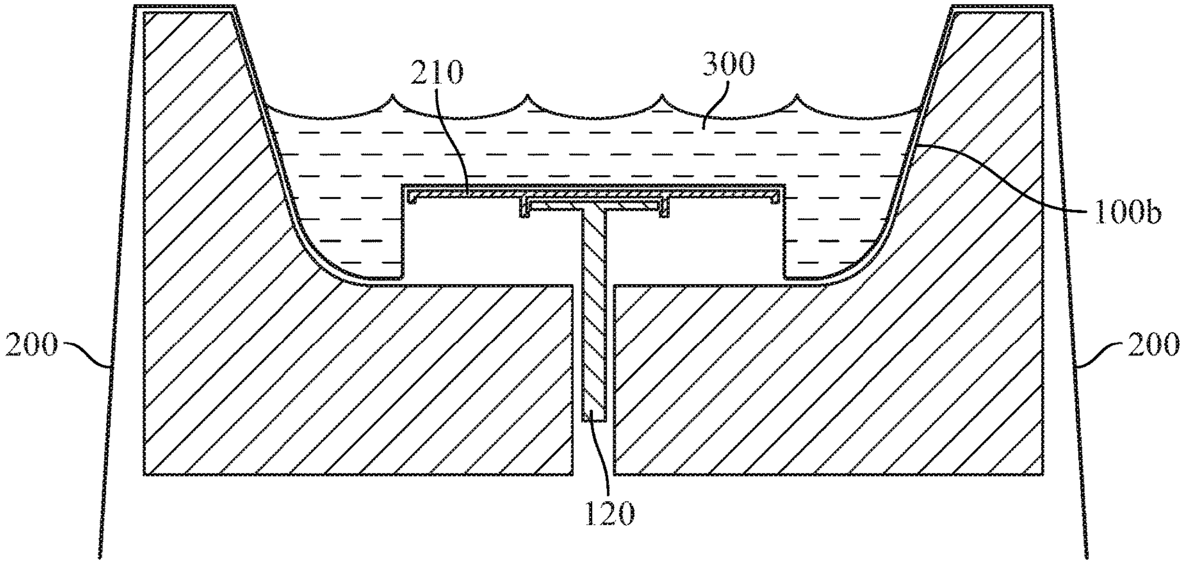
FIG. 5B is a cross-sectional view showing the same improperly placed drape as FIG. 5A but with the disk lifted to the top of its travel.

Referring to FIGS. 5A and 5B, an improperly placed drape condition is shown where the drape 200 has bunched up beneath the rigid disk 210. FIG. 5A shows this condition with the lifting rod 120 mechanism in the down position, and FIG. 5B shows the same condition with the disk 210 lifted to the top of its travel. This bunching condition occurs when the drape 200 is pulled into the basin 100 during cyclic operation, preventing proper contact between the drape 200 and the basin walls. When this occurs, ice formed at the wall does not break free from the drape/wall interface and continues to build up until there are hard frozen chunks of saline at the walls.

The present disclosure addresses this problem by providing attachment elements integrated into the sterile drape assembly that interface with corresponding attachment points on the slush machine top surface. The attachment elements maintain the drape 200 in proper position throughout the slush production cycle, eliminating the need for periodic operator intervention.

Figure 6A:
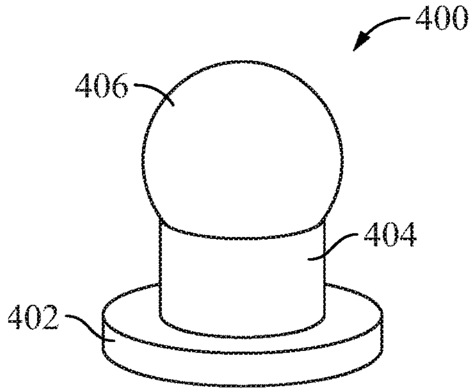
FIG. 6A is an isometric view of a button stud according to a preferred embodiment of the present disclosure showing the base, cylindrical post, and spherical head.

Referring to FIG. 6A, a button stud 400 according to the present disclosure is shown. The button stud 400 comprises a base 402, a cylindrical post 404 extending upward from the base 402, and a head 406 at the top of the cylindrical post 404. In the preferred embodiment shown in FIG. 6A, the head 406 is spherical. The spherical head 406 of the button stud 400 creates an undercut region between the head 406 and the cylindrical post 404, which allows mating snap-clip components to flex over the larger head 406 and then engage securely around the smaller diameter cylindrical post 404. The button stud 400 may be manufactured from plastic, metal, or other suitable materials and may be permanently mounted to the machine top surface or removably attached.

Figure 6B:
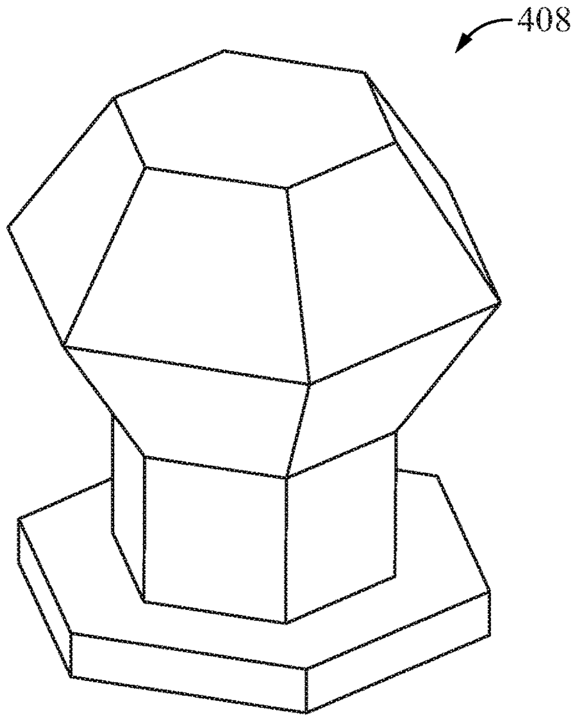
FIG. 6B is an isometric view of a polygon stud according to an additional embodiment of the present disclosure showing a base, post, and a polygon head configuration.
Figure 6C:
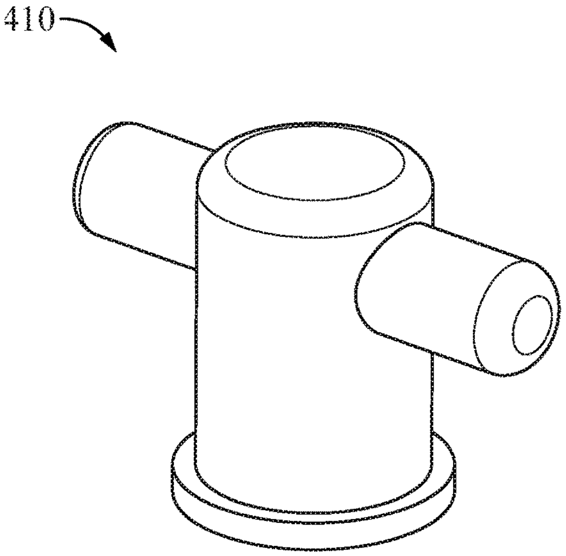
FIG. 6C is an isometric view of a cross-post stud according to an additional embodiment of the present disclosure showing a base, post and cross rod configuration.

FIGS. 6B and 6C illustrate additional embodiments of a stud, showing the base, post, and head having varying configurations.

Referring to FIG. 6B, an alternative stud embodiment is shown having a polygon-shaped head. The polygon stud 408 is provided as an example of an alternative head geometry, and one skilled in the art, given the disclosed preferred embodiments, could devise other similar geometries to produce similar snap-fit configurations based on the present disclosure. A snap-clip configured to engage with the polygon stud post 408 would be substantially similar to the preferred embodiment snap-clip 600 shown in FIG. 8A, as the key functional requirement remains that the stud have at least two different cross-sectional dimensions to enable the snap-fit engagement.

Referring to FIG. 6C, an alternative stud embodiment is shown having a cross-post configuration. The cross-post stud 410 is provided as an example of an alternative stud geometry that engages with a twist-clip 626 shown in FIG. 8B, and one skilled in the art, given the disclosed embodiments, could devise other similar geometries to produce similar twist-clip configurations based on the present invention. A twist-clip configured to engage with the cross-post stud 410 is functionally similar to the embodiment of the twist-clip 626 shown in FIG. 8B, as the key functional requirement remains with the need to provide studs with geometries that lock and/or releases a clip depending on the relative rotational position of the clip and stud. One skilled in the art, given the disclosed embodiments, could also devise a stud configured with threads and a clip configured with internal threads utilizing a nut or nut-like portion that provides the key functional requirements of both a locked and unlocked engagement based on the relative rotational position of the two components.

Figure 7:
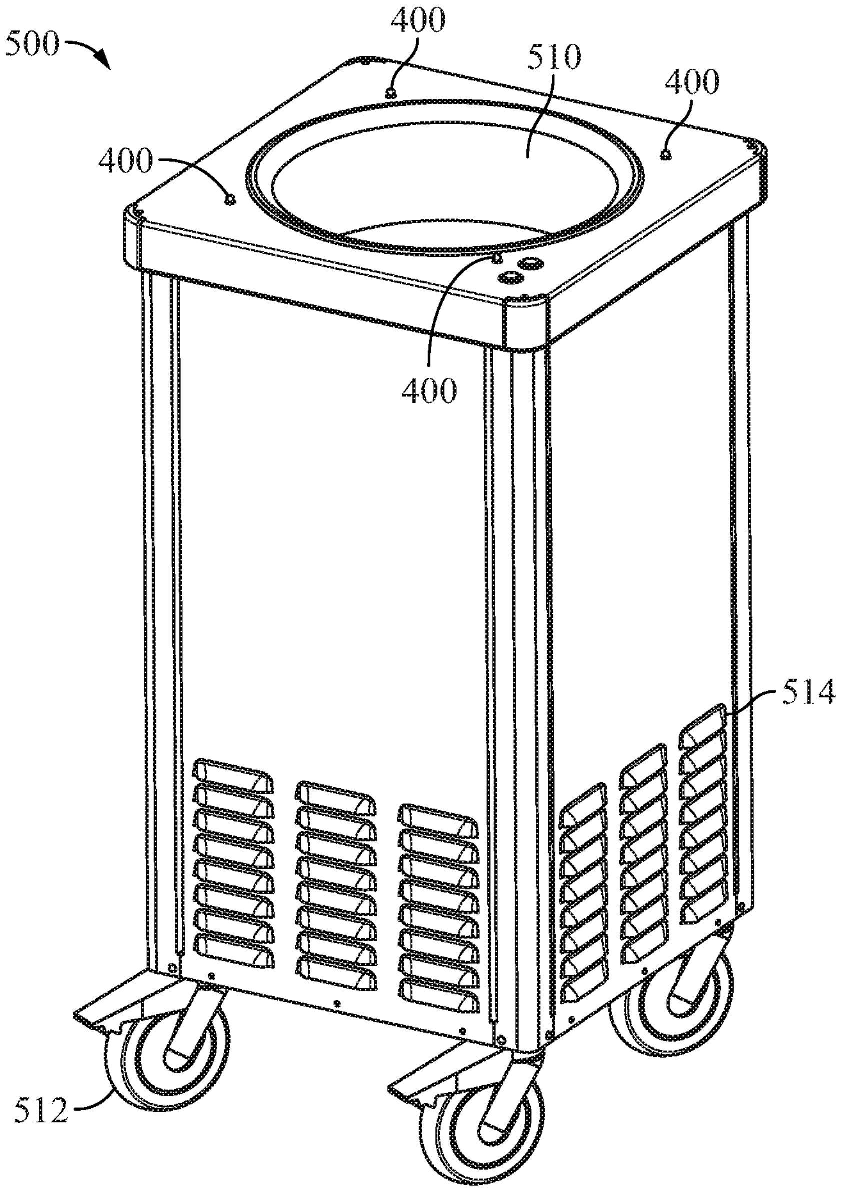
FIG. 7 is an isometric view of a slush machine cabinet with casters and ventilation, showing the basin aperture and button studs on the top surface.

Referring to FIG. 7, the slush machine cabinet 500 is shown in an isometric view. The cabinet 500 has a generally rectangular box-like structure supported by four casters 512 at its base for mobility within the operating room. The top surface of the cabinet 500 features a circular basin aperture 510 configured to receive the basin 100. Ventilation louvers 514 are provided on the sides of the cabinet 500 for air circulation required by the refrigeration system housed within. One or more of the button studs 400 are mounted on the top surface of the slush machine cabinet 500 surrounding the basin aperture 510. In a preferred embodiment, four button studs 400 are positioned at locations corresponding to the snap-clip attachments on the sterile drape assembly, with the button studs 400 arranged symmetrically around the basin 100.

Figure 8A:
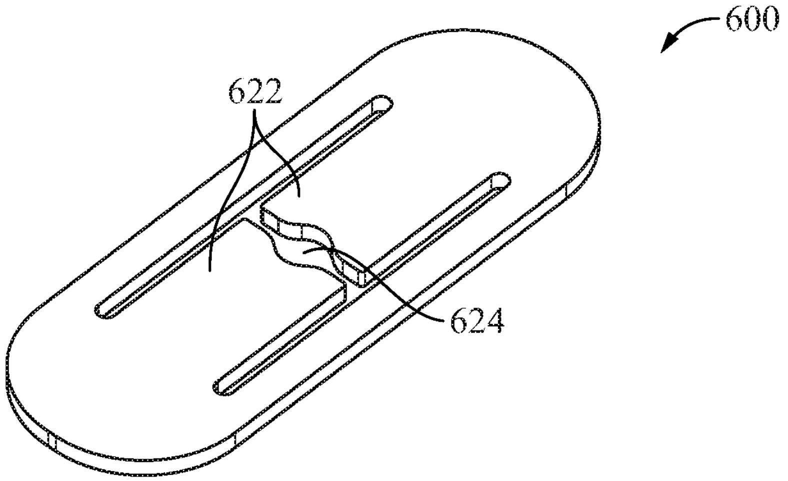
FIG. 8A is an isometric view of an elongated snap-clip attachment showing the central aperture and flexible tabs.
Figure 9A:
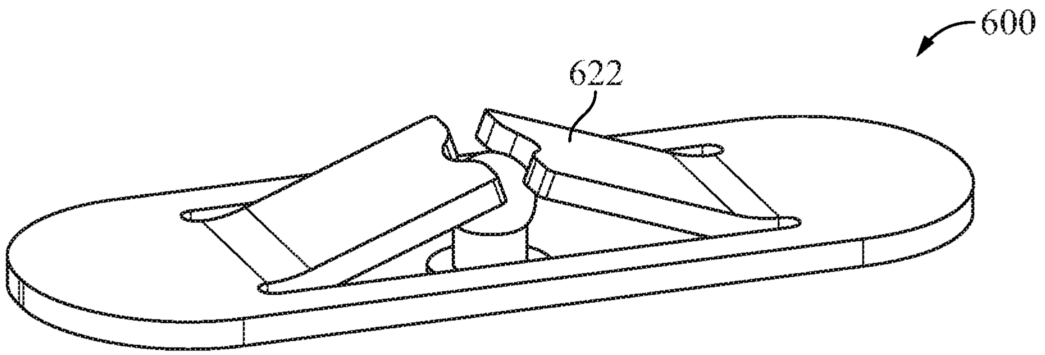
FIG. 9A shows the tabs on the snap-clip flexing upward as the snap-clip is pressed over the button stud during engagement.

Referring to FIG. 8A, an elongated snap-clip attachment 600 is shown in detail. The snap-clip attachment 600 comprises a body having a central aperture 624 and one or more of flexible tabs 622 extending from the central aperture 624. The flexible tabs 622 are configured to flex outwardly when pressed over the head 406 of the button stud 400, as shown in FIG. 9A, and return to an original position to engage around the cylindrical post 404, as in FIG. 9B. The curved edges at the end of the tabs 622 form segments of a circle. The diameter of this circle is smaller than the major diameter of the head 406 on the end of the button stud 400. The diameter is approximately the same as the diameter of the cylindrical post 404 under the head 406. This dimensional relationship ensures that the tabs 622 must flex outwardly to pass over the head 406 but then snap securely into engagement around the cylindrical post 404. This snap-clip and button stud arrangement resists lateral movement of the drape 200 during machine operation while providing easy vertical movement required for the snap-clip 600 to engage during drape placement and snap-clip disengagement for drape removal at the end of a procedure.

Figure 8B:
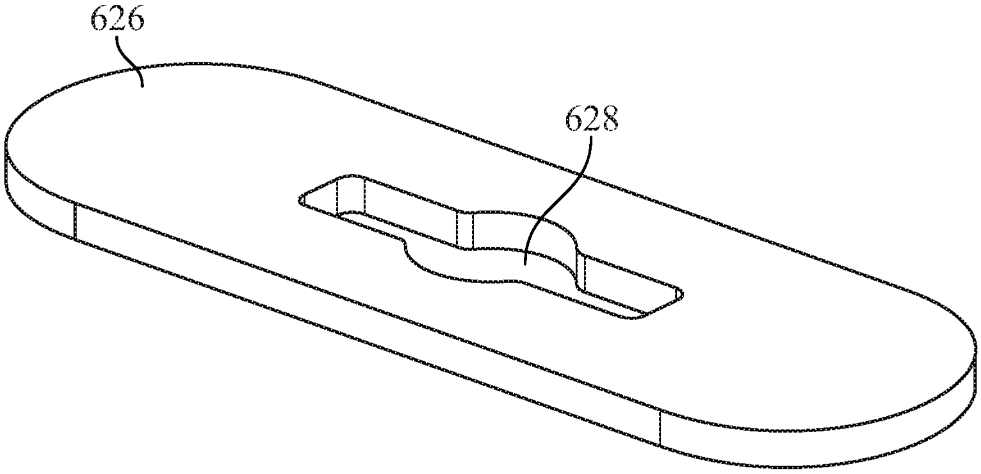
FIG. 8B is an isometric view of an elongated twist-clip attachment showing the shaped central aperture.

Referring to FIG. 8B, an alternate clip attachment is shown in detail. The twist-clip attachment 626 comprises a body having a shaped central aperture 628, where the shape of the aperture allows engagement with the cross-post stud 410 shown in FIG. 6C. After placing over the cross-post stud 410, as shown in FIG. 9C, the twist-clip attachment 626 is turned ninety-degrees securing it to the post 410, as in FIG. 9D.

Figure 9B:
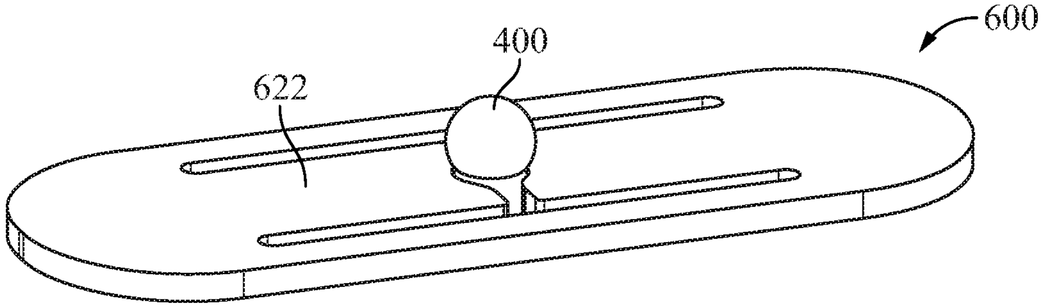
FIG. 9B shows the snap-clip in place on the button stud with the tabs returned to their original position.

Referring to FIGS. 9A and 9B, a snap-clip engagement sequence is shown. FIG. 9A shows the tabs 622 on the snap-clip 600 flexing upward as the snap-clip 600 is pressed downward over the button stud 400. FIG. 9B shows the snap-clip 600 in place on the button stud 400 with the tabs 622 of the snap-clip 600 returned to their original un-flexed position. This engagement can be accomplished by pressing downward on the top surface of the drape 200 directly above each snap-clip 600 and button stud 400 location, with no need to touch the drape 200 below the top surface of the machine.

Figure 9C:
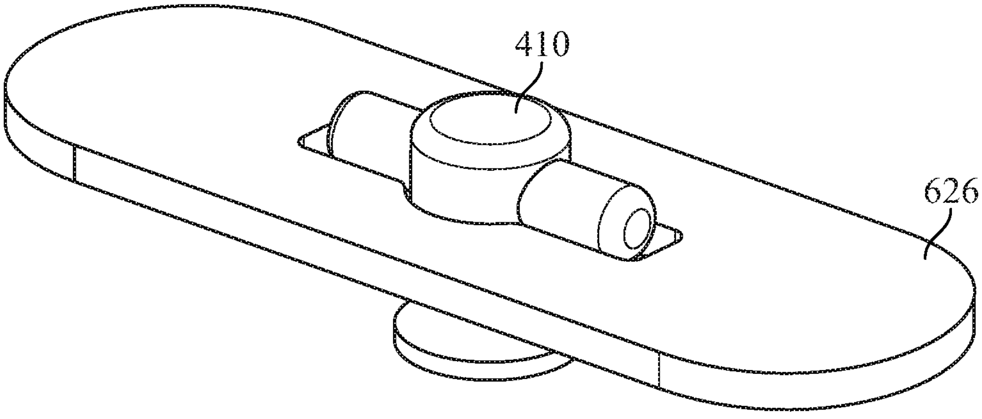
FIG. 9C shows the cross-post stud engaging the twist-clip attachment during engagement.
Figure 9D:
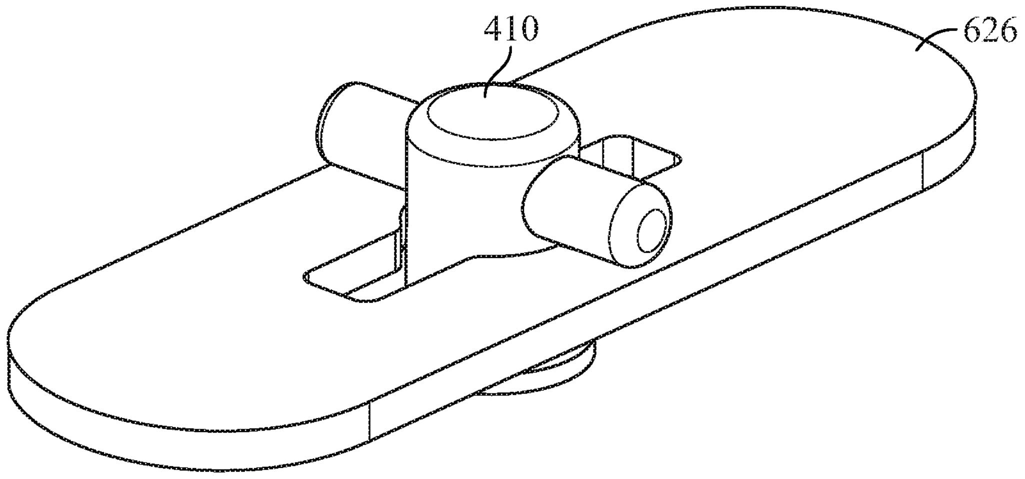
FIG. 9D shows the twist-clip attachment in the locked position on the cross-post stud.

Referring to FIGS. 9C and 9D, a twist-clip engagement sequence is shown. FIG. 9C shows the cross-post stud 410 engaging the twist-clip attachment 626 as the twist-clip is lowered downward over the cross-post stud 410. FIG. 9D shows the twist-clip attachment 626 in place on the cross-post stud 410 with the twist-clip in a ninety-degree locked position from original engagement position. This engagement can be accomplished by contacting only the top surface of the drape 200 directly above each twist-clip 626 and cross-post stud 410 location, with no need to touch the drape 200 below the top surface of the machine. In the locked position, the horizontal rod of the cross-post 410 is now perpendicular to the shaped central aperture 628, thereby preventing the twist-clip attachment 626 from being lifted off the cross-post stud 410. Since forces on the drape during operation tend to be mostly in the radial direction, the twist-clip remains in the locked position throughout the slush production cycle. This twist-clip and cross-post stud arrangement provides an alternative to the snap-clip and button stud arrangement that achieves similar lateral restraint of the drape on the machine top surface.

More specifically, there are at least two possibilities regarding the design and utility of the twist-clip. In one embodiment, the cross-post stud is fixed and non-rotating. The twist-clip is twisted 90 degrees to align with the cross-post. During placement the twisted-clip is "twisted back" 90 degrees to ensure it is locked in place. It is also possible that the cross-post stud could be designed so that it could rotate. The twist-clip in this instance would be lowered into the cross-post while the cross-post stud is rotated and after the twist clip is in place the cross-post would be rotated to a locked position. Both configurations achieve the same functional result of securing the drape 200 at the machine top surface perimeter while permitting installation and removal entirely from the top surface of the machine. The twist-clip is normally heat sealed in the drape with its long axis perpendicular to a line drawn from the center of the central rigid disk 210 and extending radially outward. When the cross-post stud is fixed and non-rotating, it is attached to the machine with the horizontal bar orientated radially toward the center of the basin. As shown, FIG. 9C is the position of the twist-clip for either installation or removal. FIG. 9D shows the twisted-clip in the locked or secured position.

Referring to FIGS. 10A, 10B, and 10C, alternative clip embodiments are shown in isometric views. Embodiment 10A shows a rectangular base 630 with rounded corners featuring a four-pronged clip element with spherical terminations at each prong end, creating four points of engagement with a button stud 400. Embodiment 10B depicts a circular base 632 with a three-pronged or tri-lobed clip configuration arranged in a triangular pattern, providing three-point engagement. Embodiment 10C shows an elongated oval base 634 with a four-pronged clip arrangement oriented along the longer axis. All three embodiments share the common characteristic of having flexible prongs or tabs that extend from a flat base, with the prongs designed to flex and snap over a button stud 400 to secure the drape 200 in proper position. The selection of a particular clip embodiment may depend on manufacturing considerations, desired engagement force, and compatibility with specific stud configurations.

Referring to FIGS. 11A and 11B, a top plan view of a transparent sterile drape 200 is shown laid flat on a surface. The drape 200 is made of clear, flexible plastic material that allows visualization of components attached to its underside. At the center of the drape 200 is the rigid disk 210 that serves as the attachment point for coupling to the lifting mechanism. The disk 210 appears as a generally circular component with a central coupling feature. Surrounding the central disk 210 and positioned at various locations on the drape 200 are the snap-clip attachments 600 which are secured to the underside of the transparent drape material. The snap-clips 600 may be attached to the underside of the sterile drape 200 by heat sealing at the appropriate location relative to the rigid disk 210. Other methods of attaching the snap-clips 600 may be used, such as gluing or using adhesive tape. In the illustrated embodiment, four snap-clip attachments 600 are distributed around the drape 200 at strategic positions relative to the central disk 210 to provide balanced securement when engaged with corresponding button studs 400. FIG. 11B provides a close-view of the placement of snap-clip attachments 600 around the central disk 210 of the sterile drape 200.

As stated above, FIG. 11A is a top-down view of a transparent sterile drape laid flat showing the central rigid disk and snap-clip attachments secured to the underside of the drape while FIG. 11B provides a close-up view of the central rigid disk and snap-clip attachments secured to the underside of the drape.

Referring to FIGS. 12A, 12B, and 12C, the slush machine cabinet 500 is shown in operation with the sterile drape 200 properly installed and filled with saline slush 300. The transparent flexible drape 200 lines the basin 100, with the drape 200 material extending upward and outward from the basin opening. The drape 200 is secured in position around the perimeter of the machine's top surface by the twist-clip attachments 600 engaged with the button studs 400. Within the drape-lined basin 100, a quantity of white crystalline slush 300 is visible, indicating that the freezing process has successfully converted the liquid saline into the desired slush consistency. The slush 300 has a granular, ice-like texture that is smooth and free of large hard clumps, demonstrating proper slush formation enabled by the drape 200 maintaining its proper position during slush production.

FIG. 12C shows a close-up view of the twist-clip attachment 600 secured to the underside of the transparent drape 200 and engaged with a corresponding button stud 400 on the machine's top surface. This engagement prevents the drape 200 from being pulled down into the basin 100 during the cyclic lifting and lowering operations.

In operation, the sterile drape assembly 200 is placed on the slush machine cabinet 500 using sterile technique. A scrubbed team member handles the drape 200 by cuffing the drape material over sterile gloves as recommended by AORN Guidelines Section 4.2.3. The drape 200 is positioned over the machine cabinet 500 with the rigid disk 210 centered over the basin 100 aperture. The rigid disk 210 is then coupled to the lifting rod 120 by snapping the disk 210 onto the rod 120. The snap-fit connection between the disk 210 and the rod 120 provides a secure but releasable coupling that allows the disk 210 to move with the rod 120 during the cyclic lifting operation.

The snap-clip attachments 600 are then engaged with the button studs 400 by pressing downward on the top surface of the drape 200 directly above each snap-clip location. As downward pressure is applied, the flexible tabs 622 of each twist-clip 600 flex outwardly as they pass over the spherical head 406 of the button stud 400. Once the tabs 622 clear the spherical head 406, they return to their original position and engage around the cylindrical post 404, locking the twist-clip 600 in place. This engagement can be accomplished by only touching the top surface of the drape 200, with no need to touch the drape 200 below the top surface of the machine, thereby maintaining compliance with sterile technique protocols including AORN Guidelines Sections 4.2.5 and 4.3. This installation method adheres to the fundamental principle that the top of a sterile, draped table is the only portion considered sterile, and that any item extending or falling below the table edge is considered non-sterile.

Once the drape 200 is placed on the machine and the snap-clips 600 are engaged with the button studs 400, sterile liquid saline is poured into the drape-lined basin 100. The saline fills the basin area with the drape 200 conforming to the basin walls and bottom. As the machine operates, the lifting rod 120 cyclically raises and lowers the disk 210 and attached drape 200. In the lowered position, the drape 200 contacts the chilled basin walls, enabling heat transfer from the saline through the drape 200 to the refrigerated basin surface. In the raised position, the drape 200 flexes away from the basin walls, causing ice crystals to be dislodged and released into the bulk fluid.

The snap-clips 600 engaged with the button studs 400 resist the lateral forces that would otherwise cause the drape 200 to be pulled into the basin 100 during the cyclic lifting operation. The snap-fit engagement between the twist-clips 600 and the button studs 400 provides sufficient resistance to lateral movement while still allowing the vertical flexing motion of the drape 200 required for proper slush formation. This maintains the drape 200 in proper position throughout the slush production cycle, enabling unattended production of smooth, clump-free surgical slush 300 without requiring periodic operator intervention to reposition the drape 200.

At the conclusion of the surgical procedure, the drape 200 can be removed by pulling upward on the drape 200 with sufficient force to disengage the twist-clips 600 from the button studs 400. The upward force causes the flexible tabs 622 to flex outwardly, allowing the twist-clips 600 to release from the button studs 400. Alternatively, if cross-post studs 410 and twist-clips 626 are used, the twist-clips 626 are rotated to disengage the attachment and lifted off of the cross-post 410. The drape 200 with the used slush can then be disposed of according to hospital protocols for medical waste. The studs remain on the machine cabinet 500 for use with subsequent sterile drape assemblies.

We claim:

1. A sterile drape assembly for use with a surgical slush production machine having a basin configured to hold a sterile liquid and a lifting mechanism, said drape assembly comprising:

- a flexible sterile drape sized and configured to conform to an interior surface of said basin;
- a rigid disk attached to a central portion of said flexible sterile drape, said rigid disk configured to releasably couple with said lifting mechanism; and
- one or more clip attachments secured to an underside of said flexible sterile drape at positions radially outward from the rigid disk, each of said one or more clip attachments configured to releasably engage with a corresponding attachment point on a top surface of said slush production machine to resist lateral movement of said drape during cyclic operation of said lifting mechanism;
- wherein said corresponding attachment point comprises a head and a post;
- wherein each of said one or more clip attachments comprises a body having a central aperture and one or more flexible tabs extending from said central aperture, said one or more flexible tabs configured to flex outwardly when pressed over said corresponding attachment point and return to an original position to engage said corresponding attachment point; and
- wherein said one or more flexible tabs have curved edges that form segments of said central aperture having a diameter smaller than a head diameter of said corresponding attachment point and equal to or greater than a post diameter of said corresponding attachment point.

2. The sterile drape assembly of claim 1, wherein said one or more clip attachments are configured to be engaged with said attachment points by pressing downward on a top surface of said flexible sterile drape without requiring contact with any portion of said flexible sterile drape below said top surface of said machine.

3. The sterile drape assembly of claim 1, wherein said one or more clip attachments and said rigid disk are integrally formed as a unitary component that is attached to said flexible sterile drape.

4. The sterile drape assembly of claim 1, wherein said one or more clip attachments comprises four clip attachments arranged symmetrically about said rigid disk.

5. The sterile drape assembly of claim 1, wherein said one or more clip attachments are heat sealed, glued, or attached with adhesive tape to said underside of said flexible sterile drape.

6. The sterile drape assembly of claim 1, wherein said rigid disk has a circular shape and includes a central coupling mechanism configured to snap onto a lifting rod of said lifting mechanism.

7. The sterile drape assembly of claim 1, wherein said flexible sterile drape is transparent.

8. The sterile drape assembly of claim 1, wherein said clip attachments are positioned on said flexible sterile drape such that when said flexible sterile drape is placed over said surgical slush production machine, each of said one or more clip attachments aligns with a corresponding head with a polygon shape and post mounted on said top surface of said machine surrounding said basin.

9. A method of installing a sterile drape on a surgical slush machine while maintaining sterile technique, said method comprising:

providing a sterile drape assembly having a flexible sterile drape, a rigid disk attached to a central portion of said sterile drape, and one or more clip attachments secured to an underside of said sterile drape at positions radially outward from said rigid disk;

positioning said sterile drape assembly over said surgical slush machine having a basin, a lifting rod, and one or more studs on a top surface of said surgical slush machine;

coupling said rigid disk to said lifting rod; and engaging said one or more clip attachments with said one or more studs by touching a top surface of said sterile drape assembly without touching any portion of said sterile drape assembly below said top surface of said surgical slush machine, thereby maintaining compliance with sterile technique protocols;

wherein said one or more clip attachments comprise flexible tabs configured to flex outwardly upon being pressed over heads of said one or more studs and the flexible tabs configured to return to unflexed position upon being passed through said heads of said one or more studs.

10. The method of claim 9, wherein said sterile technique protocols include a recommendation not to move a portion of a sterile surgical drape that establishes a sterile field after initial placement.

11. The method of claim 9, wherein said sterile technique protocols include considering areas below a level of an instrument tabletop to be contaminated.

12. The method of claim 9, wherein said engaging step is performed by a scrubbed team member without said scrubbed team member reaching over an unsterile area or contacting an unsterile surface.

* * * * *